US012742212B2

(12) United States Patent
Prince

(10) Patent No.: US 12,742,212 B2
(45) Date of Patent: Sep. 22, 2026

(54) METHOD FOR PREDICTING AND EVALUATING ANTIMICROBIAL THERAPY WHEN MOLECULAR PCR DIAGNOSTIC TESTING RESULTS YIELD MULTI-ORGANISMS AND MULTI-RESISTANT BACTERIA FROM A SINGLE DNA SAMPLE

(71) Applicant: Advanced Therapeutic Assist, Springdale, AR (US)

(72) Inventor: Robin Prince, Springdale, AR (US)

(73) Assignee: Advanced Therapeutic Assist, Springdale, AR (US)

( * ) Notice: Subject to any disclaimer, the term of this patent is extended or adjusted under 35 U.S.C. 154(b) by 9 days.

(21) Appl. No.: 17/726,855

(22) Filed: Apr. 22, 2022

(65) Prior Publication Data

US 2023/0340616 A1 Oct. 26, 2023

(51) Int. Cl.

*G16H 20/10* (2018.01)
*C12Q 1/689* (2018.01)
*G16B 20/00* (2019.01)
*G16H 10/60* (2018.01)
*G16H 50/20* (2018.01)
*C12Q 1/6888* (2018.01)

(52) U.S. Cl.

CPC ............. *C12Q 1/689* (2013.01); *G16B 20/00* (2019.02); *G16H 10/60* (2018.01); *G16H 20/10* (2018.01); *G16H 50/20* (2018.01); *C12Q 1/6888* (2013.01); *C12Q 2600/136* (2013.01); *C12Q 2600/16* (2013.01)

(58) Field of Classification Search

CPC ...................................................... G16H 20/10
See application file for complete search history.

(56) References Cited

U.S. PATENT DOCUMENTS

2021/0172000 A1* 6/2021 Baunoch .................. C12Q 1/08

OTHER PUBLICATIONS

Melendez et al. Real-time PCR assays compared to culture-based approaches for identification of aerobic bacteria in chronic wounds. Clin. Microbial Infect 2010, 16: 1762-1769 (Year: 2010).*

De Waele et al. How I search for a sepsis source. Critical Care 2019, 23:386, pp. 1-3 (Year: 2019).*

Forrest et al. Use of Electronic Health Records and Clinical Decision Support Systems for Antimicrobial Stewardship. (Clinical Infectious Diseases 2014, 59(S3), S122-33) (Year: 2014).*

Evans et al. A computer-assisted management program for antibiotics and other antiinfective agents. The New England Journal of Medicine 1998, vol. 338, No. 4, pp. 232-238 (Year: 1998).*

Sacco et al. Inpatient beta-lactam test-dose protocol and antimicrobial stewardship in patients with a history of penicillin allergy. Ann Allergy Asthma Immunol 2019, vol. 122, pp. 184-188 (Year: 2019).*

Canovas-Segura et al. Development of a clinical decision support system for antibiotic management in a hospital environment. Prog Artif Intell 2016, 5:181-197 (Year: 2016).*

Maurin. Real-time PCR as a diagnostic tool for bacterial diseases. Expert Rev Mol Diagn 2012, 12(7), pp. 731-754 (Year: 2012).*

MacVane et al. Benefits of adding a rapid PCR-based blood culture identifiecation panel to an established antimicrobial stewardship program. Journal of Clinical Microbiology 2016, vol. 54, No. 10, pp. 2455-2463) (Year: 2016).*

Hansen WLJ, van der Donk CFM, Bruggeman CA, Stobberingh EE, Wolffs PFG (2013) A Real-Time PCR-Based Semi-Quantitative Breakpoint to Aid in Molecular Identification of Urinary Tract Infections. PLoS ONE 8(4): e61439. doi:10.1371/journal.pone.0061439.*

Sun Z, et al (2021) The Direct Semi-Quantitative Detection of 18 Pathogens and Simultaneous Screening for Nine Resistance Genes in Clinical Urine Samples by a HighThroughput Multiplex Genetic Detection System. Front. Cell. Infect. Microbiol. 11:: 660461. doi: 10.3389/fcimb.2021.660461.*

Sibhghatulla Shaikh et al. "Antibiotic resistance and extended spectrum beta-lactamases:Types, epidemiology and treatment"; Saudi Journal of Biological Sciences; Jan. 215; vol. 22(1); pp. 90-101.

Gu et al., "Rapid Pathogen Detection by Metagenomic Next-Generation Sequencing of Infected Body Fluids", Nature Medicine, Jan. 2021, vol. 27, No. 1, 26 pages.

Gunasekera et al., "Organoids and Bioengineered Intestinal Models: Potential Solutions to the Cryptosporidium Culturing Dilemma", Microorganisms, May 11, 2020, vol. 8, No. 5, 16 pages.

* cited by examiner

*Primary Examiner* — Joseph Woitach
(74) *Attorney, Agent, or Firm* — Maier & Maier, PLLC

(57) ABSTRACT

A method for predicting and evaluating antimicrobial therapy for patient specific molecular results when molecular testing yields multi-organism and multi-resistant bacterial. Essential in the fight against antimicrobial resistance is the effective use of antibiotics. An exemplary method provides healthcare providers a therapeutic guide for optimizing patient outcomes by significantly improving antibiotic stewardship by using resistant gene enzymes to guide antibiotic therapy most likely to succeed.

24 Claims, 3 Drawing Sheets

WOUND ANALYSIS 100

| Facility Information 102 | Patient Information 104 | Specimen Information 106 |
| --- | --- | --- |
| **Facility Name:** test family practice<br>**Provider:** Dr Sample<br>**Phone:**<br>**Fax:** | **Name:** Knotwell, Ima<br>**DOB:** 02/02/1976<br>**Gender:** Female | **Lab Accession#:** 345612<br>**Date Collected:** 02/17/2022<br>**Date Received by Lab:**<br>**Date Reported:**<br>**Specimen Type:** WOUND |

Positive Organisms Detected 108

| Organism | Estimated Copies/mL | Estimated Microbial Load |
| --- | --- | --- |
| Corynebacterium jeikeium, striatum, tuberculostear | 50,000 | Low |
| Enterococcus faecalis | 2,100,000 | High |
| Klebsiella pneumoniae, oxytoca | 1,700,000 | High |
| Peptoniphilus harei, ivorii | 310,000 | Moderate |
| Peptostreptococcus anaerobius, asaccharolyticus, m | 310,000 | Moderate |
| Prevotella bivia | 300,000 | Moderate |

Resistance Genes Detected 110

| Gene Description |
| --- |
| **sul (1,2)**<br>These genes are associated with potential resistance to Sulfonamide antibiotics. |
| **TEM 1, TEM 2, through TEM 30. ***<br>ESBL: This gene is associated with potential resistance to Penicillins and First/Second Generation Cephalosporins. |

* These are highlighted to reflect detection of ESBL's, Methicillin Resistance, or Vancomycin Resistance please use special precautions in these patients.

Fig. 1

| First Line Medications 202 | | | |
|---|---|---|---|
| **Medication** | **Route** | **Dose** | **Consideration** |
| Amoxicillin-Clavulanate | PO | 875/125mg bid x7-14 days | Enterococcus, Klebsiella, Prevotella, Peptoniphilus, Peptostreptococcus Adjust dose CrCl < 30 mL/min. Avoid use with penicillin allergy. |
| **Alternative Medications 204** | | | |
| **Medication** | **Route** | **Dose** | **Consideration** |
| Levofloxacin | PO | 500-750mg PO/IV qd x7-14 days | Enterococcus, Klebsiella, Peptoniphilus, Peptostreptococcus Black box warning for tendinitis and tendon rupture, peripheral neuropathy, and CNS effects in elderly - anxiety, confusion, depression, hallucinations. . Second line use for acute sinusitis, acute bronchitis, and uncomplicated UTI . Avoid in ages below 16. Avoid in pregnancy. adjust dose CrCl <50min/ml. Can cause C difficile |
| **Other Options 206** | | | |
| Metronidazole | PO | 500mg tid x 7-10 days | Prevotella, Peptoniphilus, Peptostreptococcus Avoid alcohol use during and 24hrs after treatment. Caution if hepatic impairment. May cause metallic-like taste. Often causes yeast infections. |
| **Medication** | **Route** | **Dose** | **Consideration** |
| Moxifloxacin | PO | 400mg qd x7-14 days | Enterococcus, Klebsiella, Prevotella, Peptoniphilus, Peptostreptococcus Black box warning for tendinitis and tendon rupture, peripheral neuropathy, and CNS effects in elderly - anxiety, confusion, depression, hallucinations. . Second line use for acute sinusitis, acute bronchitis, and uncomplicated UTI . Avoid in ages below 16. Avoid in pregnancy. Can cause C difficile. |

Fig. 2

METHOD FOR PREDICTING AND EVALUATING ANTIMICROBIAL THERAPY WHEN MOLECULAR PCR DIAGNOSTIC TESTING RESULTS YIELD MULTI-ORGANISMS AND MULTI-RESISTANT BACTERIA FROM A SINGLE DNA SAMPLE

FIELD

The embodiments generally relate to a method for assisting health care providers in predicting and evaluating antimicrobial therapy from reverse transcription-polymerase chain reaction (RT-PCR) testing when multiple organisms and resistance is detected. An exemplary embodiment may provide targeted antibiotic selections, specific to each patient, superior to other empirical therapy.

BACKGROUND

Antibiotic resistance is a problem of deep scientific concern both in hospital and community settings. (Sibhghatulla Shaikh et al., "Antibiotic resistance and extended spectrum beta-lactamases: Types, epidemiology and treatment", Saudi Journal of Biological Sciences (2014), 22(1): 90-101). The rapid emergence of resistant bacteria is occurring worldwide, endangering the efficacy of antibiotics. This crisis has been attributed to the misuse and overuse of antibiotics. The CDC and other organizations and experts recommend improving microbial identification and optimizing therapeutic regimens, among other actions, to combat this current crisis. As often as 50% of the time, antibiotics are being prescribed either unnecessarily or incorrectly. These findings highlight the need for quick and accurate pathogen identification, as well as the use of genetic markers for antibiotic resistance detection.

Production of extended-spectrum β-lactamases (ESBLs) is a significant resistance-mechanism that impedes the antimicrobial treatment of infections caused by ESBL-E and is a serious threat to the currently available antibiotic armory.

ESBLs are classified into several groups according to their amino acid sequence homology. The hydrolysis of B-lactam antibiotics by β-lactamases is the most common mechanism for resistance for this class of antibacterial agents especially in the Gram-negative bacteria. This med class is the preferred treatment regimen for many infectious diseases and may play a critical role in appropriate therapy. The rise in antibiotic resistance has been significantly documented by CDC. Extended Spectrum Beta-lactamase *Enterobacter* (ESBL-E) increased by 53% in the United States from 2012 to 2017 due to increase in community acquired infections. ESBL-E are enzymes that inactivate most penicillin's, cephalosporins, and aztreonam. Another rise has been seen in ESBL-CTX, this resistance can harbor in any gram negative organism but is most prevalent in *E. coli, Klebsiella*, and *Proteus* species. ESBL-CTX are enzymes which hydrolyze cefotaxime more efficiently than ceftazidime and are mostly encoded by transferable plasmids. This group of ESBL's confer resistance to Penicillin, cephalosporins, and Aztreonam. A third group, ESBL-carbapenem resistance (CRE) has been declared by the CDC as a serious threat. Data from 2017 report concludes that ESBL-CRE caused 13,000 hospitalizations and 1,100 deaths in 2017. Extended Spectrum Beta-lactamase-CRE inactivates carbapenems. Carbapenems are considered as last-resort antibiotics for the treatment of infections caused by multidrug-resistant Gram-negative bacteria. With the increasing use of carbapenems in clinical practice, the emergence of carbapenem-resistant pathogens now poses a new threat to human health. Currently, antibiotic options for the treatment of carbapenem-resistant Enterobacteriaceae (CRE) are very limited, when B-lactams are removed from therapy there are only a few options of therapy left, polymyxins, Tigecycline, Fosfomycin, and aminoglycosides. This exemplary method provides a new way to approach this class of drugs based on combination of the Ambler and Bush-Jacoby classification schemes.

A polymerase chain reaction (PCR) test is a diagnostic that can rapidly determine infection by analyzing a sample to see if it contains genetic material for presence of bacteria, viruses, fungus, or parasites. There are many different nucleic acid test technologies available, such as Real-Time PCR technology, a Qualitative test. Qualitative tests are well suited for the detection of microorganisms in specimens whose presence, at any level, is associated with a disease state. This process may be known as reverse transcription (RT). The RT-PCR technology can make multiple copies or amplification of DNA segment to determine presence of organisms. PCR is 99% accurate in organism identification and gene resistance detection. RT-PCR diagnostic test can be performed rapidly and accurately. PCR has the ability for broader identification of DNA targets including fungal, anaerobic, and other atypical microbes. More importantly, it has the ability to detect multiple organisms and multiple resistance in a single DNA sample in a short period of time. One limitation with PCR technology is while testing for multiple organisms presented on single sample is very beneficial, the ability to derive an exact quantitative measure is very difficult.

Therefore, amplification curve-based calculations can be used to provide accumulative averages to give quantitative ranges of low, moderate, or high. qPCR will be different from culture and sensitivity MIC's. RT-PCR may be more sensitive and more accurate in showing the presence of microbes per sample, and thus assessment of all information found on the PCR test may be interpretated and evaluated before antibiotic therapy is administered. The quantitative amplification is helpful to the prediction process to evaluate the organisms as pathogenic, normal flora, or potential colonized. The resistant gene markers detected allow therapy to be guided in a more targeted approach, superior to empirical treatments of past. PCR genotypic may be used as a testing tool for an exemplary embodiment.

SUMMARY

An exemplary embodiment may assist healthcare providers in pharmacotherapy choices when multi-gene detection and multi-organism detection is found using RT-PCR technology. An exemplary method predicts antibiotic selections specific to each patient by eliminating the antibiotic med class or classes most likely to fail based on (i) comprehensive organisms detected, (ii) mapping of the potential resistance found, (iii) links to the clinical significance of the resistance found to organism detected, and (iv) the clinical assessment of patient as applied, to predict and evaluate the most appropriate antibiotic therapy. By combining clinical information with threat of resistance towards the pathogen or pathogens detected, providers can quickly pinpoint the best antibiotics to succeed for that specific patient with confidence thus using best antimicrobial stewardship process available.

An exemplary treatment may be based on the classification, assessment and clinical relevance of the multiple resistance genes found by PCR technology. Assessment and evaluation of the resistance genes found may be essential to the method. A molecular PCR machine can be programmed to detect a limited number of known resistant gene enzymes. There are also hundreds of strains and substrates within each known resistant gene identified. There are 2 important things to decide once resistant gene is detected positive:

First, the resistance may be determined as clinically relevant or not clinically relevant to the pathogen or pathogens detected. The PCR technology does not provide this automatically from the DNA sample tested. In high-complexity PCR testing, the detection of organisms and detection of resistance are not directly related to the clinical relevance. An exemplary method may link the resistance to organisms as clinically relevant by using statistical data that has measured resistance based on individual research models and manufactures protocols of what the machine has been programed to detect. Other models do not perform this critical step.

Second, an exemplary method maps the resistant gene substrates to associated med classes statistically found to be successful. More significantly, an exemplary embodiment may provide a systematic approach to uniquely classify the Beta-Lactam med classes. This new classification system of the Beta-Lactams is an improvement over standard empirical guidelines because an exemplary method may have proven ways to overcome resistance, the method recommends oral therapy first before promoting intravenous therapy either as monotherapy or combination therapy.

In an exemplary embodiment, the resistance in the B-lactams can be grouped by strains within categories based on antibiotic med class most likely to succeed. Automatic removal of antibiotics simply due to detection of certain resistant genes may be problematic when it comes to the beta-lactam family of antibiotics. This med class of antibiotics makes up the majority of antibiotic therapy available today. Therefore, an embodiment may map the resistant genes to appropriate med class by the method of classification to predict which pharmacotherapy to keep or eliminate.

An exemplary embodiment implements beta-lactam antibiotics using a superior process than the prior art. The classification of beta-lactamases enzymes is essential for predicting target resistant therapy. The B-lactam antimicrobial agents exhibit the most common therapy prescribed in Gram negative bacterial infections and seem to be a prominent cause of resistance. An exemplary classification allows providers to use more oral options in the community care setting before having to initiate IV therapy, which is a major departure from standard use of the Sandford Guide or IDSA guidelines that use empirical therapy applied to Culture and Sensitivity testing.

An Exemplary Method Used to Classify Beta-Lactams:

Extended Spectrum (ESBL):

TEM, SHV and CTX-M groups: —These genes may associated with resistance to Penicillins, Monobactam, First-third Generation Cephalosporins. Third generation cephalosporins in combination with beta-lactamase inhibitor can overcome resistance.

SHV groups: Pooled 1-200 substrates—An exemplary embodiment may respond to multi detection SHV. These genes may be associated with resistance to all Beta-Lactams when in the presence of KPC otherwise. Third generation cephalosporins in combination with beta-lactamase inhibitor can overcome this ESBL otherwise and SHV-1 can incorporate third generation cephalosporins.

TEM groups: pooled—TEM,1-30 strains are the most common. These genes are associated with resistance to Penicillins, First and Second Cephalosporins. Third generation cephalosporins up to fifth generation cephalosporins and beta-lactamase inhibitors will overcome this ESBL. TEM substrates above TEM-30 are rare, but these genes follow the CTX recommendation, and TEM-50 are very rare, and begin therapy with carbapenems and carbapenems with inhibitors.

Minor Spectrum (ESBL):

PER, VEB, GES-1—These rare genes are associated with resistance to Penicillins, First to Third gen Cephalosporins, and Monobactams. Same as CTX to overcome ESBL.

NDM, IMP, VIM, GES, OXA, PER-2 and KPC may indicate Carbapenem Resistant Enterobacteriaceae (CRE ESBL). Oxa-48, 23, 40, 58, 72, 51 may indicate a resistance overcome by Ceftazidime-Avibactam (OXA-1: exception same protocol as TEM 1-30) OXA-48 and 51 clinically relevant with *Acinetobacter* and *Pseudomonas*. IMP, NDM, and VIM may indicate a resistance overcome by Aztreonam, tigecycline, polymyxin, Fosfomycin, and Ceftazidime-Avibactam. KPC for *Klebsiella* may indicate a resistance overcome by Ceftazidime-Avibactam. GES for *Klebsiella* may indicate a resistance overcome by Cefepime and carbapenem with inhibitor.

ACT, MIR, FOX, and DHA groups of genes are associated with resistance to Penicillin and First and Second gen Cephalosporins. Rocephin IM may be used as loading plus inhibitor in these resistant genes before going to cefepime and carbapenems. An exemplary method may react to ACC the same as Amp C in *E. coli* or otherwise use the above protocol. An exemplary method may consider DHA as an indicator for AmpC inducers. In presence of these organisms, *Enterobacter cloacae, Serratia marcescens, Citrobacter freundii, Pseudomonas aeruginosa, Escherichia coli, Shigella species, Acinetobacter baumannii Klebsiella pneumoniae*, and *Salmonella*, which are AmpC inducers, the AmpC protocol may be followed.

AmpC genes are associated with resistance to all beta-lactams except for cefepime and carbapenems. In presence of these organisms, *Enterobacter cloacae, Serratia marcescens, Citrobacter freundii, Pseudomonas, Proteus aeruginosa, Escherichia coli, Shigella species, Acinetobacter baumannii Klebsiella pneumoniae, Salmonella*. If AmpC is detected in combination with other genes such as FOX, MIR, or ACT, and it cannot be determined if the ampC is dominant, then an exemplary method may use a loading dose of Rocephin plus an inhibitor.

An exemplary embodiment provides a step method to determine best pharmacotherapy by uniquely incorporating clinical data of the patient with the laboratory data of patient to predict the most appropriate antibiotic therapy for each patient by eliminating potential ineffective antimicrobial drug classes. An exemplary method provides excellent antimicrobial stewardship guidance to combat the current antibiotic crisis. Examples of valuable clinical assessment may include age, gender, environmental setting, source of infection, location of infection, sample type used, clinical presentation of patient in office, clinical notes associated with disease states, co-morbidities, immune status, and patient history.

An exemplary method may identify all organisms positive on a PCR test result from a single biological sample. An embodiment may further assess organisms into categories by bacterial, fungal, parasitic, or viral microbials. Qualitative tests may be best suited for the detection of microorganisms in specimens whose presence, at any level, is associated with a disease state. If a fungal, parasitic, or viral organism is detected and the patient is symptomatic, then therapy may be used. For bacteria organisms detected, use the analysis of the amplification linear curve provided to help determine when antibiotic intervention is appropriate. Bacteria found can be pathogenic, normal flora, or colonized in sample.

quantitative range provided by PCR test result may be used to determine if bacterial organism detected is pathogenic, normal flora, or colonization by using both qualitative and quantitative measures. Amplification curve-based calculations can be used to provide accumulative averages to give quantitative ranges of low, moderate, or high. Therapy may be applied if patient is symptomatic, and the range of detection falls in a moderate level. Some exceptions may apply to very young, very old, and immunocompromised patients. An exemplary method may therefore assess the resistant genes found for clinical relevance with organisms found, as described above in the embodiments.

The patient's date of birth may be considered in an exemplary method. Age may play a role in therapy dosing and duration. In the elderly, elimination of an antibiotic med class may be necessary simply based on side effects. Age also can help determine assumed immune status of that patient. Pediatrics, age 12 and below, and elderly, age 85 and above, may be used by this method as exceptions to normal adult parameters and therapy may be initiated at a lower quantitative range.

An exemplary embodiment may also consider the patient's gender. Gender may determine therapy duration and dose. For example, urinary infections are considered chronic infections in men while they are considered acute infections in women. Gender can play a role when analyzing therapies in different panels; Men's health, Women's health, urine, vaginal.

An exemplary method may take into consideration the location of infection by Panel Type. The location of the infection is important to establish what is normal flora (organisms that should be there in a healthy patient). Sometimes, normal flora can be the cause of the infection if elevated. The location of infection also tells us whether gram positive or gram negatives are considered more serious or the dominant source of infection for that region of the body. The location of the infection can help guide in antibiotic choices simply based on the pharmacokinetics of the drug's response in that region. Panel categories may include urine, wound, nail, derma, gastro, women's health, men's health, and respiratory.

An exemplary embodiment may take into consideration the source of sample (e.g., tissue, bone, swab, urine, stool). The source of the sample and how the sample was collected may be important in the evaluation of intervention with antibiotics. For example, *Staph aureus* from a nose swab may be colonized and therefore may not warrant antibiotic intervention unless found in an elevated range. However, *Staph aureus* in a wound sample that may be considered MRSA should be evaluated for antibiotic intervention at any range. Another issue to remember with sample collection is primary verses secondary source. For example, BV found in a urine result will be quantitatively lower than same BV found on vaginal swab. Another example would be the difference of wound sample by swab verses tissue or bone. Therefore, the source of the sample must play a role in determining when antibiotic therapy should be initiated.

An exemplary embodiment may identify the environmental setting of patient. Settings such as community care, long term care, and hospital care may influence the choice of therapy. Considerations may include insurance coverage, availability of drugs to the patient, cost, and where the drug is going to be administered. The setting may also be a good indicator of the severity of the infection. Oral therapy in combination over more expensive monotherapies will steer therapy to affordable antibiotics and thus more cost effective and more insurance coverage. The right therapy at the right time can prevent hospital administration and save thousands of healthcare dollars.

ICD-10 code and ICD code description is the clinical assessment of patient from providers clinical assessment in clinic. This code may provide an indication from the provider of the probable cause of infection which can guide therapy choices.

An exemplary embodiment may eliminate medicines based on the allergies of patient and remove all drug med classes that the patient may be allergic from final therapy recommendations.

Clinical Notes from physician may be considered. Clinical notes may modify therapy including, but not limited to, immunocompromised, renal function, dialysis, catheter patient, co-morbidities, pregnant, drug interactions, and others. Patient may be symptomatic for organism to be considered infectious. Therefore, clinical markers may be important. For example: fever, chills, warfarin, amiodarone, post-surgery, immune compromised, cancer, diabetes, etc. . . . . Clinical notes can help determine the target therapy personalized for that specific patient.

Finally, the above variables can be assessed in combination to eliminate all antibiotic med drug class unlikely to succeed based on potential resistance detected, clinical data present, and any known allergies. To assess the dosing and duration of pharmacotherapy to include higher doses, longer durations, or combination therapy to overcome resistance found. Acute dosing, chronic dosing, or aggressive pathogen dosing should be considered in this step.

The mapping of the resistant genes detected by PCR technology may be based on the qualitative detection of that resistant enzyme. Known resistant genes enzymes can be used to map resistance to a specific bacterial organism using PCR technology. When multiple organisms are detected, it may be useful to have a common knowledge of resistant genes enzymes and the known antimicrobial med class affected by that resistance as well as the bacterial organisms most likely to be linked to that resistance. When clinical relevance is determined for a particular organism or pathogen, the choice may be between removal of that antibiotic med class from therapy or use of combination therapy to overcome the resistance or longer duration of therapy in some cases.

BRIEF DESCRIPTION OF THE DRAWINGS

Advantages of embodiments of the present invention will be apparent from the following detailed description of the exemplary embodiments. The following detailed description should be considered in conjunction with the accompanying FIGURES in which:

Exemplary FIG. 1 shows a urine therapeutic guidance of a patient.

Exemplary FIG. 2 shows a wound therapeutic guidance of a patient.

Exemplary

DETAILED DESCRIPTION OF THE EMBODIMENTS

Figure 3:
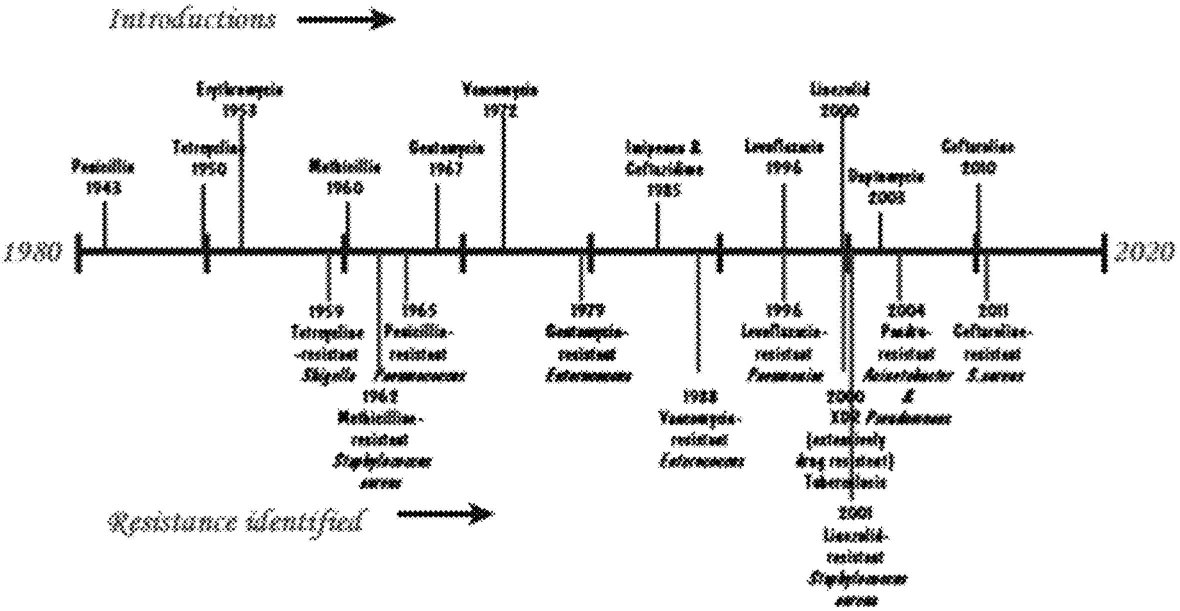
FIG. 3 illustrates a timeline indicating drug developments versus antibiotic resistance discoveries.

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

As used herein, the word “exemplary” means “serving as an example, instance or illustration.” The embodiments described herein are not limiting, but rather are exemplary only. It should be understood that the described embodiments are not necessarily to be construed as preferred or advantageous over other embodiments. Moreover, the terms “embodiments of the invention”, “embodiments” or “invention” do not require that all embodiments of the invention include the discussed feature, advantage or mode of operation.

The following are common markers of resistance which may be useful to see represented on an Infectious Disease PCR diagnostic test. These may be required to properly address Antibiotic Stewardship.

TABLE 1

| Med class: | Resistant Genes: |
|---|---|
| Penicillin and Cephalosporin resistance | ACT, MIR, FOX |
| AmpC resistance | DHA, ACC, AmpC |
| Extended- B-lactamases resistance | CTX-M Groups, TEM and SHV |
| Minor Extended -B-lactamases resistance | PER-1, VEB, GES-1 |
| CRE B-lactamases | IMP, NDM, VIM, OXA, KPC, GES, PER2 |
| Sulfonamide resistance | SUL |
| Trimethoprim resistance | DFR |
| Macrolide and Lincomycins | ErmA, ErmB, ermC, MefA |
| Aminoglycoside resistance | Aa, Acc, A6 |
| Tetracycline resistance | TetM, TetB |
| Quinolone resistance | QnrA, QnrS, QnrB, and Gyrase groups |
| Methicillin resistance | MecA |
| Vancomycin resistance | VanA and VanB |
| Polymycin resistance | Mcr- |

In the embodiments, by applying an exemplary method, a customized antimicrobial therapeutic guidance prediction can be produced and submitted back to health care providers to help provide the best individualized Antibiotic Stewardship program to the patients.

An exemplary embodiment may use a reverse transcription-polymerase chain reaction (RT-PCR) test to identify all the organisms in a biological sample.

An exemplary embodiment may relate to the ATA-CHOICE™ method to determine patient specific antimicrobial therapy from PCR multi-resistant gene detection and PCR multi-organism identification.

An exemplary embodiment may provide improved pharmacotherapy with most effective antibiotic stewardship for each specific patient sample, by using additional patient data to accurately utilize the embodiments. This data may include personal data, such as date of birth, and gender of patient. The data may further include the environmental setting of a patient, such as hospital, community, and LTC setting. The data may further include the clinical assessment or ICD-10 code and descriptions from provider. The data may further include drug allergies of that specific patient when provided.

An exemplary method may first interpret a PCR laboratory result findings and identify the presence of all positive organisms. The identified organisms may be placed into categories of microbials by fungal, bacterial, viral, or other. Therapy is appropriate for any level detection if disease state is present, but to further protect the best antibiotic stewardship an exemplary embodiment may use the quantitative amplification curve provided by each laboratory as part of the equation to find the organism most likely to be the cause of infection.

Fungal, Viral, or parasite positive detection may require intervention, but the bacterial gram positives and gram negatives organisms may also be assessed by these steps to ensure pathogens exist and therapy is warranted.

Second, an exemplary embodiment may evaluate the quantitative range of the bacterial organism provided by the PCR result. To determine if an organism is pathogenic and likely to cause infection, an embodiment may analyze the low, moderate, high ranges provided. For example, anything above 50,000 copies per microliter amplified in machine may be labelled as infectious. The exceptions to this rule may apply to immune compromised, very young, or very old patients and to aggressive known pathogens. *Pseudomonas* may be considered pathogenic at a lower quantitative range due to the aggressive nature of the organism. Normal flora may be considered pathogenic when quantitative range is found at a moderate to high level. Thus, if a patient is symptomatic and the quantitative load is moderate to high then consider the organism to be infectious or pathogenic as basic rule of thumb.

Third an exemplary embodiment may determine for any positive resistance gene detected, a link to the pathogen, and may adjust pharmacotherapy accordingly. Next, an exemplary embodiment may begin clinical assessments to eliminate any ineffective antimicrobials. Age or date of birth, gender, environmental setting, sample source, panel type, ICD-10 codes, allergies, co-morbidities, dialysis, catheter patients, prothesis patients, pregnancy, and many other variables may be considered as provided herein. Next, an exemplary embodiment may eliminate all antimicrobial drug classes that are least likely to succeed and may provide or predict an effective therapy.

An exemplary embodiment may provide an assessment of the resistant gene enzyme. Resistance is real and new antibiotics are not being developed fast enough. So more than ever it is very important to preserve all of the current antibiotics on the market to the best of our ability. There is strong scientific data to suggest that we are in an antimicrobial resistance crisis. For this reason, PCR is a great tool in our toolbox to help detect potential resistance. As to the pharmacotherapy, the most widely used classification of β-lactamases is the Ambler classification (Table 2) that divides β-lactamases into four classes (A, B, C and D) based upon their amino acid sequences. The other classification is the Bush Jacoby “Functional Classification of B-Lactamases where the substrate and inhibitor profiles group the enzymes based on similar phenotypes. The embodiments apply both of these classifications to predict pharmacotherapy by developing a hybrid classification of B-Lactamases of the two methods combined.

Ambler Classification: β-lactamases

| Ambler Class | β -Lactamase Type | Preferred Substrates | Representative Enzymes |
|---|---|---|---|
| A | Narrow spectrum | Penicillins, narrow-spectrum cephalosporins | TEM-1, TEM-2, SHV-1 |

-continued

| Ambler Class | β -Lactamase Type | Preferred Substrates | Representative Enzymes |
|---|---|---|---|
| A | Extended Spectrum | Narrow- and extended-spectrum β-lactams | SHV-2, CTX-M-15, PER-1, VEB-1 |
| A | Serine-carbapenemase | Carbapenems | KPC-1, IMI-1, SME-1 |
| B | Metallo-β-lactamases | Most β-lactams, including carbapenems | VIM-1, IMP-1, NDM-1 |
| C | Cephalosporinases | Cephalosporins | AmpC, P99, ACT-1, CMY-2, FOX-1, MIR-1 |
| D | OXA-type enzymes | Penicillins, oxacillins, carbapenems | OXA enzymes |

Table 3 shows other common resistant gene enzymes and the corresponding antibiotic med class affected.

TABLE 3

| Antimicrobial Med Class | Representative Enzymes |
|---|---|
| Penicillin and Cephalosporin resistance: | ACT, MIR, FOX, ACC, DHA, CMY, CFE |
| Penicillin, Cephalosporins, Monobactams, and Carbapenems: | AmpC |
| Extended- B-lactamases resistance: | CTX-M Group, TEM, and SHV |
| Minor Extended -B-lactamases resistance: | PER, VEB, GES-1 |
| Carbapenem resistance: | IMP, NDM, VIM, OXA, KPC, GES |
| Sulfonamide resistance: | SUL |
| Trimethooprim resistance: | DFR |
| Macrolide and Lincomycins: | ErmA, ErmB, ErmC, MefA |
| Aminoglycoside resistance: | Aa, Acc, A6 |
| Tetracycline resistance: | TetM, TetB |
| Quinolone resistance: | QnrA, QnrS, QnrB, and Gyrase groups |
| Methicillin resistance: | MecA |
| Vancomycin resistance: | VanA and VanB |
| Polymycin resistance: | Mcr |

Table 4 may provide common organisms with potential known resistance corresponding to resistant genes according to an exemplary embodiment.

TABLE 4

| | |
|---|---|
| Amino-glycosides | *Acinetobacter*, *Citrobacter*, *Enterobacter*, *E coli*, *Klebsiella*, *Proteus*, *Pseudomonas*, *Salmonella*, *Serratia* |
| AmpC | *Enterobacter cloacae*, *Serratia marcescens*, *Citrobacter freundii*, *Pseudomonas aeruginosa*, *Escherichia coli*, *shigella* species, *Acinetobacter baumannii*, *Klebsiella pneumoniae*, *Salmonella*, and *Proteus* |
| CTX-M group | *Acinetobacter*, *Citrobacter*, *Enterobacter*, *E coli*, *Klebsiella*, *Proteus*, *Morganella*, *Pseudomonas*, *Salmonella*, *Serratia*, *Shigella* |
| Erm A | *Enterococcus faecium*, *Staph aureus*, *Staph Epi* |
| Erm B | *Acinetobacter*, *B fragilis*, *Chlamydia*, *Enteroccocus*, *Ecoli*, *Kleb*, *Staph aureus*, *S saprophyticus*, *Strep B*, *Strep pneumo*, and *Strep pyrogenes*, *Citrobacter*, *Corynebacterium*, *Clostridium*, *fusobacterium*, *H influenza*, *gonnorrhea*, *Peptostrep*, *Pseudomonas*, *Salmonella*, *Shigella*, *Vibrio* |
| Erm C | *Staph aureus*, *Staph Epi* |
| TEM | *Ecoli*, *Vibrio*, *Enterobacter* sp. *Kleb*, *Proteus*, *Salmonella*, *Serratia*, *H influenza*, |
| Gyrase A | *Ecoli* and *Shigella* only |
| KPC | *Kleb* only |
| QnrB, QnrS, QnrA1-A2 | *Citrobacter*, *Enterobacter*, *Ecoli*, *Kleb*, *Salmonella*, *Shigella*, *Vibrio*, *Serratia* |
| SHV | *Ecoli*, *Vibrio*, *Enterobacter* sp. *Kleb*, *Proteus*, *Salmonella*, *Serratia*, *H influenza*. |

TABLE 4-continued

| | |
|---|---|
| Sul/dfr | *Ecoli*, *Vibrio*, *Enterobacter* sp, *Kleb*, *Proteus*, *Salmonella*, *Serratia*, *H influenza*, *pseudomonas*, *providencia* |
| GES | *Kleb* only |
| Mcr-1 | *Ecoli*, *Kleb*, *Salmonella*, *Shigella* |
| PER/VEB | *Pseudomonas* |
| Oxa-1 | *Kleb*, *Ecoli*, *Pseudomonas* |
| Oxa-23, 24, 40, 51, 58, 72 | *Acinetobacter*, *Kleb*, *Ecoli*, *Proteus* |
| Oxa-48 | *Enterobacter* sp |
| IMP, NDM, VIM | *Enterobacter* sp, *Pseudomonas* |
| Van A | *Enterococcus facium* and *faecallis* and *Staph aureus* |
| Van B | *Enterococcus faecium* and *faecalis* |
| MecA | *Staph Aureus*, *Staph epi*, *Staph hemolyticus* |
| MefA | *Enterococcus*, *Gardnerella*, *Haemophilus*, *Neisseria*, *Meningitis*, *Streptococcus* sp. |
| grlA | *Ecoli* and *Shigella* only |
| Per2 | *Acinetobacter* |

Note that *Enterobacter* sp refers to the *Enterobacter* family which includes *Enterobacter cloacae, Serratia marcescens, Citrobacter freundii, Pseudomonas aeruginosa, Escherichia coli, Shigella species, Acinetobacter baumannii, Klebsiella pneumoniae, Salmonella*, and *Proteus.*

FIG. 1 is an exemplary wound analysis 100 according to an exemplary embodiment. The wound analysis 100 may identify facility 102, patient 104, and specimen 106 information. Further, the analysis 100 may identify a list of organisms positively detected 108 in the sample 106. An exemplary analysis may also identify one or more resistant genes 110 detected in the patient 104. In an exemplary embodiment, certain genes may be highlighted to reflect specific situations. For example, in FIG. 1 the TEM 1, TEM 2 through TEM 30 genes may be highlighted to reflect detection of ESBL's, methicillin resistance, or vancomycin resistance. Special precautions may be used in these patients.

Based on the exemplary analysis shown in FIG. 1, an embodiment may identify that *enterococcus* is considered normal flora in wounds and is not typically treated until upper-moderate to high copies/μL are reached. Risk factors for possible infection are recent hospitalization and/or broad-spectrum antibiotic use. Infection is often seen with mixed bacteria. Therapy options may include amoxicillin, Augmentin, levofloxacin, or linezolid. Next, an exemplary embodiment may alter the treatment based on the detection of *klebsiella*; the therapy may instead comprise augmentin/ceftriaxone or levofloxacin.

An exemplary embodiment may consider that *prevotella* is normal flora of the skin, and may apply treatment at moderate to high detection. The therapy may be updated to include Augmentin, metronidazole, or clindamycin.

*Peptostreptococcus/Peptoniphilus* is normal flora of the skin, it tends to have increased virulence with mixed bacteria. Anaerobic infection may be suspected if wound has putrid discharge. An exemplary embodiment may update the therapy to include Augmentin, clindamycin, cephalexin, doxycycline, levofloxacin, or metronidazole.

*Corynebacterium* is part of the normal human skin flora and is generally recognized as a contaminant in wound samples. An exemplary method may consider possible pathogenicity in chronic wounds or with foreign devices.

FIG. 2 is an exemplary medication or treatment order. An exemplary embodiment may identify first line medications 202 based on the PCR test, detected genes, organisms/ infections, and patient criteria. Alternative medications 204 and other options 206 may also be recommended.

An exemplary embodiment may identify all organisms in a biological sample using an RT-PCR test and may continue by categorizing each of the organisms detected as one of Fungal, Bacterial, Viral, or parasitic; and using a quantitative amplification curve associated with each organism to identify a probable cause of infection and identifying a plurality of potential resistant genes detected by the RT-PCR test and determining which potential resistant genes are clinically relevant to the probable cause of infection to eliminate a plurality of medicinal classes.

An exemplary embodiment may also asses additional variables such as a date of birth or age of the patient to adjust therapy dosing, duration, or elimination of one or more medicinal classes; a gender of the patient to determine chronic from acute infections; a source of infection by panel, wherein the panel indicates location of infection to body region; the sample source, such as one of a tissue, bone, urine, stool, other secretion source to determine a severity of infection detected; the environmental setting of patient, wherein the environmental setting is one of a community, facility, and institution; an ICD-10 code from provider; one or more allergies associated with the patient; and any clinical notes from the provider to provide a detailed patient history and clinical notes about infection. All the above can be applied to determine therapy by removing or eliminating antibiotic classes least likely to succeed. The treatment can be relayed to a pharmacy and then applied to the patient, or applied to the patient directly if possible. An exemplary method may include applying a therapy when multiple resistance is detected by PCR by overcoming resistance or eliminating med class, or combination therapy to address the potential for antimicrobial failure.

One or more known resistance indicating genes may be identified. The resistance indicating genes, as shown in the previously described tables, may include: ACT, MIR, FOX, ACC, DHA, AmpC, Mcr-1, CTX-M1, CTX-M2, CTX-M9, CTX-M8/25, dfr (A1, A5), sul (1, 2) Genes, ErmA, ErmB, ErmC, MefA, gr1A, IMP, NDM, VIM KPC, MecA, Oxa-1, Gyrase, PER-1/VEB-1/GES-1, QnrA1, QnrA2, QnrB, QnrS, PER1 and PER2, SHV combo group 1-200, SHV 2,5, TEM Group 1-30, TEM-50, TetB, TetM, VanA1, VanA2, VanB, OXA-23, OXA-24, OXA-40, Oxa-48, OXA-58, OXA-72, and OXA-51.

FIG. 3 is a timeline identifying the years in which antimicrobial medicinal classes were developed on the top and the years in which resistance to the corresponding med classes were first discovered. As shown in FIG. 4, resistance to antibiotics has increased at a rate greater than the new antibiotics have been developed, creating a need for methods to overcome resistance without using our carbapenems except as a last resort. Yes, while it is easy for providers to prescribe carbapenems for multi-detected organisms in the hope to avoid resistance is directly causing the unnecessary acceleration of carbapenem antibiotic resistance. Antibiotics paired with beta-lactamase inhibitors may provide one method for overcoming antibiotic resistance.

For example, in ACT, MIR, FOX, ACC, DHA, CTX-M, TEM, SHV, PER, VEB, GES-1, the use of a loading dose of IM Ceftriaxone with oral dose of augmentin (as an inhibitor) may provide another way to overcome the resistance problem. In KPC, OXA, IMP, NDM, VIM, the use of a beta-lactam inhibitors with a carbapenem may provide yet another way to overcome resistance. As a result, it may be appreciated that a customized therapeutic guidance based on Tables 1, 2, 3, and 4 where the organism detected with resistant identified can direct the therapy choices in the right direction by eliminating med classes least likely to succeed due to the resistance and/or therapy to overcome resistance in order to spare the last resort med class drugs. Therapeutic guidance paired with superior molecular diagnostic tools can optimize patient outcomes, reduce patient hospital admissions, and significantly improve Antibiotic Stewardship.

Thus, an exemplary embodiment may provide for (1) Assessment of organisms-Qualitative and Quantitatively; (2) Assessment of Potential Resistance; (3) Assessment of the organism detected with associated clinical relevance of resistance detected; and (4) Assessment of the clinical information of patient.

The foregoing description and accompanying FIGURES illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A method for providing a targeted therapy specific to a patient having a urinary tract infection, the method comprising:

obtaining a urine sample from the patient;

obtaining one or more clinical assessment factors selected from patient age, patient gender, source of the urine sample, environmental setting of the patient, antibiotic allergies of the patient, clinical status of the patient, and an assigned international classification of disease (ICD-10) code of the patient;

performing or having performed reverse transcription quantitative polymerase chain reaction (RT-qPCR) to detect and identify microbial organisms in the urine sample and detect and identify potential antibiotic resistance genes in the microbial organisms;

identifying one or more microbial organisms in the urine sample using the RT-qPCR, and categorizing each of the identified one or more microbial organisms as Gram-positive bacteria, Gram-negative bacteria, or fungal;

using a semi-quantitative value from the RT-qPCR associated with each identified one or more microbial organism to identify a probable cause of the infection, wherein:

(i) the probable cause of the infection is a Gram-positive bacteria or a Gram-negative bacteria when the RT-qPCR sample contains at least 50,000 copies/ml of a Gram-positive bacteria or a Gram-negative bacteria, or (ii) the probable cause of the infection is fungal;

identifying one or more potential antibiotic resistant genes in the identified one or more microbial organism by the RT-qPCR, the potential antibiotic resistance genes selected from the group consisting of CTX-M, TEM, SHV, PER, VEB, GES, IMP, NDM, VIM, OXA, KPC, SUL, DFR, ErmA, ErmB, ErmC, MefA, Aph, AAC, TetM, TetB, QnrA, QnrS, QnrB, Gyrase, MecA, MecC, VanA, VanB, Mcr, ACT, MIR, FOX, DHA, ACC, AmpC, and subtypes thereof; and when the probable cause of the infection is Gram-positive bacteria or Gram-negative bacteria, and when the identified potential antibiotic resistance genes comprises one or more of TEM, SHV, CTX-M, PER-1, VEB, GES-1, and OXA-1, applying to the patient a target therapy of one or more antibiotic based on:

(a) eliminating antibiotics most likely to fail due to the identified potential antibiotic resistance genes TEM, SHV, CTX-M, PER-1, VEB, GES-1, and OXA-1, and providing one or more antibiotic to override the potential antibiotic resistance, and (b) accounting for the one or more clinical assessments factors of the patient, wherein the target therapy eliminates penicillins, monobactams, first generation and second generation cephalosporins, and monotherapy third generation cephalosporins as likely to fail, and provides a combination of beta-lactamase inhibitor with a third generation cephalosporin to override the potential antibiotic resistance.

2. The method of claim 1, wherein the target therapy is applied non-intravenously.

3. The method of claim 1, wherein the third generation cephalosporin is applied intramuscularly, and the beta-lactamase inhibitor is applied orally.

4. The method of claim 1, wherein the target therapy provides a combination of Rocephin (ceftriaxone) and Augmentin (amoxicillin/clavulanate potassium).

5. The method of claim 1, wherein the probable cause of infection comprises Enterobacteriaceae.

6. The method of claim 1, wherein the probable cause of infection comprises *Escherichia coli.*

7. The method of claim 1, wherein when the one or more identified potential antibiotic resistance genes comprises SHV, and further comprises KPC, the target therapy eliminates penicillins, monobactams, carbapenems, and first generation to fifth generation cephalosporins except for Avycaz (ceftazidime/avibactam) as likely to fail, and provides Avycaz to override the potential antibiotic resistance.

8. The method of claim 7, wherein the probable cause of infection comprises *Klebsiella.*

9. The method of claim 7, wherein the target therapy is applied intravenously.

10. A method for providing a targeted therapy specific to a patient having a urinary tract infection, the method comprising:

obtaining a urine sample from the patient;

obtaining one or more clinical assessment factors selected from patient age, patient gender, source of the urine sample, environmental setting of the patient, antibiotic allergies of the patient, clinical status of the patient, and an assigned international classification of disease (ICD-10) code of the patient;

performing or having performed reverse transcription quantitative polymerase chain reaction (RT-qPCR) to detect and identify microbial organisms in the urine sample and detect and identify potential antibiotic resistance genes in the microbial organisms;

identifying one or more microbial organisms in the urine sample using the RT-qPCR, and categorizing each of the identified one or more microbial organisms as Gram-positive bacteria, Gram-negative bacteria, or fungal;

using a semi-quantitative value from the RT-qPCR associated with each identified one or more microbial organism to identify a probable cause of the infection, wherein:

(i) the probable cause of the infection is a Gram-positive bacteria or a Gram-negative bacteria when the RT-qPCR sample contains at least 50,000 copies/ml of a Gram-positive bacteria or a Gram-negative bacteria, or (ii) the probable cause of the infection is a fungal;

identifying one or more potential antibiotic resistance genes selected from the group consisting of CTX-M, TEM, SHV, PER, VEB, GES, IMP, NDM, VIM, OXA, KPC, SUL, DFR, ErmA, ErmB, ErmC, MefA, Aph, AAC, TetM, TetB, QnrA, QnrS, QnrB, Gyrase, MecA, MecC, VanA, VanB, Mcr, ACT, MIR, FOX, DHA, ACC, AmpC, and subtypes thereof;

when the probable cause of the infection is Gram-positive negative or Gram-negative bacteria, and when the identified potential antibiotic resistance genes comprise one or more of NDM, IMP, and VIM, applying to the patient a target therapy of one or more antibiotic based on:

(a) eliminating antibiotics most likely to fail due to the potential antibiotic resistance genes NDM, IMP, and VIM, and providing one or more antibiotic to override the potential antibiotic resistance, and (b) accounting for the one or more clinical assessment factor of the patient, wherein the target therapy eliminates penicillins, carbapenems, and first generation to fifth generation cephalosporins except for Avycaz (ceftazidime/avibactam) and Aztreonam (monobactam) as likely to fail, and provides one or more of Avycaz and Aztreonam to override the potential antibiotic resistance.

11. The method of claim 10, wherein the probable cause of the infection comprises Enterobacteriaceae.

12. The method of claim 10, wherein the target therapy is applied intravenously.

13. A method for providing a targeted therapy specific to a patient having a urinary tract infection, the method comprising:

obtaining a urine sample from the patient;

obtaining one or more clinical assessment factors selected from patient age, patient gender, source of the urine sample, environmental setting of the patient, antibiotic allergies of the patient, clinical status of the patient, and an assigned international classification of disease (ICD-10) code of the patient;

performing or having performed reverse transcription quantitative polymerase chain reaction (RT-qPCR) to detect and identify microbial organisms in the urine sample and detect and identify potential antibiotic resistance genes in the microbial organisms;

identifying one or more microbial organisms in the urine sample using the RT-qPCR, and categorizing each of the identified one or more microbial organisms as Gram-positive bacteria, Gram-negative bacteria, or fungal;

using a semi-quantitative value from the RT-qPCR associated with each identified one or more microbial organism to identify a probable cause of the infection, wherein:

(i) the probable cause of the infection is a Gram-positive bacteria or a Gram-negative bacteria when the RT-qPCR sample contains at least 50,000 copies/ml of a Gram-positive bacteria or a Gram-negative bacteria, or (ii) the probable cause of the infection is a fungal;

identifying one or more potential antibiotic resistance genes selected from the group consisting of CTX-M, TEM, SHV, PER, VEB, GES, IMP, NDM, VIM, OXA, KPC, SUL, DER, ErmA, ErmB, ErmC, MefA, Aph, AAC, TetM, TetB, QnrA, QnrS, QnrB, Gyrase, MecA, MecC, VanA, VanB, Mcr, ACT, MIR, FOX, DHA, ACC, AmpC, and subtypes thereof;

when the probable cause of the infection is Gram-positive negative or Gram-negative bacteria, and when the identified potential antibiotic resistance genes comprise one or more of OXA-48 and OXA-51, applying to the patient a target therapy of one or more antibiotic based on:

(a) eliminating antibiotics most likely to fail due to the potential antibiotic resistance genes OXA-48 and OXA-51, and providing one or more antibiotic to override the potential antibiotic resistance and (b) accounting for the one or more clinical assessment factor of the patient, wherein the target therapy eliminates penicillins, monobactams, carbapenems, and first generation to fifth generation cephalosporins except for Avycaz (ceftazidime/avibactam) as likely to fail, and provides Avycaz to override the potential antibiotic resistance.

14. The method of claim 13, wherein the probable cause of infection comprises Enterobacteriaceae.

15. The method of claim 13, wherein the probable cause of the infection comprises one or more of *Acinetobacter* sp. and *Pseudomonas* sp.

16. The method of claim 13, wherein the target therapy is applied intravenously.

17. A method for providing a targeted therapy specific to a patient having a urinary tract infection, the method comprising:

obtaining a urine sample from the patient;

obtaining one or more clinical assessment factors selected from patient age, patient gender, source of the urine sample, environmental setting of the patient, medicinal allergies of the patient, clinical status of the patient, and an assigned international classification of disease (ICD-10) code of the patient;

performing or having performed reverse transcription quantitative polymerase chain reaction (RT-qPCR) to detect and identify microbial organisms in the urine sample and detect and identify potential antibiotic resistance genes in the microbial organisms;

identifying one or more microbial organisms in the urine sample using the RT-qPCR, and categorizing each of the identified one or more microbial organisms as Gram-positive bacteria, Gram-negative bacteria, or fungal;

using a semi-quantitative value from the RT-qPCR associated with each identified organism to identify a probable cause of the infection, wherein:

(i) the probable cause of the infection is a Gram-positive bacteria or a Gram-negative bacteria when the RT-qPCR sample contains at least 50,000 copies/ml of a Gram-positive bacteria or a Gram-negative bacteria, or (ii) the probable cause of the infection is fungal;

identifying one or more potential antibiotic resistance genes selected from the group consisting of CTX-M, TEM, SHV, PER, VEB, GES, IMP, NDM, VIM, OXA, KPC, SUL, DFR, ErmA, ErmB, ErmC, MefA, Aph, AAC, TetM, TetB, QnrA, QnrS, QnrB, Gyrase, MecA, MecC, VanA, VanB, Mcr, ACT, MIR, FOX, DHA, ACC, AmpC, and subtypes thereof;

when the probable cause of the infection is Gram-positive or Gram-negative bacteria, and when the identified potential antibiotic resistance genes are one or more of ACT, MIR, FOX, and DHA, applying to the patient a target therapy of one or more antibiotic based on:

(a) eliminating antibiotics most likely to fail due to the potential antibiotic resistance genes ACT, FOX, MIR, and DHA, and providing one or more antibiotic to override the potential antibiotic resistance, and (b) accounting for the one or more clinical assessment factor of the patient, wherein the target therapy eliminates penicillins, monobactams, first generation, second generation, and monotherapy third generation cephalosporins as likely to fail, and provides a combination of beta-lactamase inhibitor with a third generation cephalosporin to override the potential antibiotic resistance.

18. The method of claim 17, wherein the target therapy is applied non-intravenously.

19. The method of claim 17, wherein the target therapy provides a combination of Rocephin (ceftriaxone) and Augmentin (amoxicillin/clavulanate potassium).

20. A method for providing a targeted therapy specific to a patient having a urinary tract infection, the method comprising:

obtaining a urine sample from the patient;

obtaining one or more clinical assessment factors selected from patient age, patient gender, source of the urine sample, environmental setting of the patient, medicinal allergies of the patient, clinical status of the patient, and an assigned international classification of disease (ICD-10) code of the patient;

performing or having performed reverse transcription quantitative polymerase chain reaction (RT-qPCR) to detect and identify microbial organisms in the urine sample and detect and identify potential antibiotic resistance genes in the microbial organisms;

identifying one or more microbial organisms in the urine sample using the RT-qPCR, and categorizing each of the identified one or more microbial organisms as Gram-positive bacteria, Gram-negative bacteria, or fungal;

using a semi-quantitative value from the RT-qPCR associated with each identified organism to identify a probable cause of the infection, wherein:

(i) the probable cause of the infection is a Gram-positive bacteria or a Gram-negative bacteria when the RT-qPCR sample contains at least 50,000 copies/ml of a Gram-positive bacteria or a Gram-negative bacteria, or (ii) the probable cause of the infection is fungal;

identifying one or more potential antibiotic resistance genes selected from the group consisting of CTX-M, TEM, SHV, PER, VEB, GES, IMP, NDM, VIM, OXA, KPC, SUL, DFR, ErmA, ErmB, ErmC, MefA, Aph, AAC, TetM, TetB, QnrA, QnrS, QnrB, Gyrase, MecA, MecC, VanA, VanB, Mcr, ACT, MIR, FOX, DHA, ACC, AmpC, and subtypes thereof;

when the probable cause of the infection is Enterobacteriaceae and the identified potential antibiotic resistance genes comprises AmpC, or when the probable cause of the infection is *Escherichia coli* and the identified potential antibiotic resistance genes comprises ACC, applying to the patient a target therapy of one or more antibiotic based on:

(a) eliminating antibiotics most likely to fail due to the potential antibiotic resistance genes AmpC or ACC, and providing one or more antibiotic to override the potential antibiotic resistance, and (b) accounting for the one or more clinical assessment factor of the patient, wherein the target therapy eliminates penicillins, monobactams, carbapenems, and first generation, second generation, and third generation cephalosporins, except for Cefepime, Avycaz (ceftazidime/avibactam), and Ceftaroline as likely to fail, and provides one or more of Cefepime, Avycaz, and Ceftaroline to override the potential antibiotic resistance.

21. The method of claim 20, wherein the target therapy is applied intravenously.

22. The method of claim 20, wherein when the one or more identified potential antibiotic resistance genes comprises AmpC, and further comprises MecA, the target therapy provides Ceftaroline to override the potential antibiotic resistance.

23. A method for providing a targeted therapy specific to a patient having a urinary tract infection, the method comprising:

obtaining a urine sample from the patient;

obtaining one or more clinical assessment factors selected from patient age, patient gender, source of the urine sample, environmental setting of the patient, antibiotic allergies of the patient, clinical status of the patient, and an assigned international classification of disease (ICD-10) code of the patient;

performing or having performed reverse transcription quantitative polymerase chain reaction (RT-qPCR) to detect and identify microbial organisms in the urine sample and detect and identify potential antibiotic resistance genes in the microbial organisms;

identifying one or more microbial organisms in the urine sample using the RT-qPCR, and categorizing each of the identified one or more microbial organisms as Gram-positive bacteria, Gram-negative bacteria, or fungal;

using a semi-quantitative value from the RT-qPCR associated with each identified one or more microbial organism to identify a probable cause of the infection, wherein:

(i) the probable cause of the infection is a Gram-positive bacteria or a Gram-negative bacteria when the RT-qPCR sample contains at least 50,000 copies/ml of a Gram-positive bacteria or a Gram-negative bacteria, or (ii) the probable cause of the infection is a fungal;

identifying one or more potential antibiotic resistance genes selected from the group consisting of CTX-M, TEM, SHV, PER, VEB, GES, IMP, NDM, VIM, OXA, KPC, SUL, DFR, ErmA, ErmB, ErmC, MefA, Aph, AAC, TetM, TetB, QnrA, QnrS, QnrB, Gyrase, MecA, MecC, VanA, VanB, Mcr, ACT, MIR, FOX, DHA, ACC, AmpC, and subtypes thereof;

when the probable cause of the infection is Enterobacteriaceae and when the identified potential antibiotic resistance genes comprise one or more of OXA-23, OXA-24, OXA-40, OXA-58, and OXA-72, applying to the patient a target therapy of one or more antibiotic based on:

(a) eliminating antibiotics most likely to fail due to the potential antibiotic resistance genes OXA-23, OXA-24, OXA-40, OXA-58, and OXA-72, and providing one or more antibiotic to override the potential antibiotic resistance, and (b) accounting for the one or more clinical assessment factor of the patient, wherein the target therapy eliminates penicillins, monobactams, carbapenem, and first generation to fifth generation cephalosporins except for Avycaz (ceftazidime/avibactam), as likely to fail, and provides Avycaz (ceftazidime/avibactam) to override the potential antibiotic resistance.

24. The method of claim 23, wherein the probable cause of infection comprises Enterobacteriaceae.

* * * * *